United States Patent [19]
Rosenberg

[11] Patent Number: 5,554,154
[45] Date of Patent: Sep. 10, 1996

[54] INTRA-OSSEOUS NEEDLE DRILL

[76] Inventor: Norman Rosenberg, 11122 Alford, Brighton, Mich. 48116

[21] Appl. No.: 397,779

[22] Filed: Mar. 3, 1995

[51] Int. Cl.⁶ .................................................. A61B 17/00
[52] U.S. Cl. .............................. 606/80; 606/79; 606/180; 606/167
[58] Field of Search ................................. 606/79, 80, 86, 606/180, 185, 88, 96–102, 167, 170; 433/165, 114, 76

[56] References Cited

U.S. PATENT DOCUMENTS

| | | | |
|---|---|---|---|
| 2,419,045 | 4/1947 | Whittaker | 606/180 |
| 3,120,845 | 2/1964 | Horner | 606/80 |
| 3,173,417 | 3/1965 | Horner | 606/180 |
| 4,867,158 | 9/1989 | Sugg | 606/80 |
| 5,207,697 | 5/1993 | Carusillo et al. | 606/167 |
| 5,431,655 | 7/1995 | Melker et al. | 606/185 X |

*Primary Examiner*—Corrine M. McDermott
*Assistant Examiner*—N. Kent Gring
*Attorney, Agent, or Firm*—Gifford, Krass, Groh, Sprinkle, Patmore, Anderson & Citkowski

[57] ABSTRACT

A drill for a medical needle having a fitting end and a tip suitable for intra-osseous use includes a chuck extending outwardly from a hand-held housing, the chuck including means for releasably receiving the needle at it fitting end. Energy storage means disposed within the housing couple rotational energy to the chuck and attached needle upon activation of a housing-supported switch. Energy storage may either be electrical, in which case the housing includes therein a battery and motor mechanically coupled to the chuck, and an electrical switch having operative connections to the motor and battery. The battery is preferably rechargeable and an optional inductive pick-up may be disposed within the housing along with power-conversion circuitry enabling the battery to be inductively charged. In an alternative embodiment the drill includes mechanical energy storage means in the form of a wind-up spring mechanically coupled to the chuck, and wherein the switch allows energy stored in the spring to be released to rotate the chuck and needle attached thereto.

11 Claims, 3 Drawing Sheets

INTRA-OSSEOUS NEEDLE DRILL

FIELD OF THE INVENTION

The present invention relates generally to intra-osseous cavity entry, and, more particularly, to a drill to which a suitable needle may be removably attached to expedite penetration into the intra-osseous cavity for blood draw, infusion of IV fluids, antibiotics and other medications.

BACKGROUND OF THE INVENTION

Although direct circulatory system entry is the most efficient method by which to draw blood, introduce medications, carry out transfusions, and the like, there are times when the procedure is highly impractical. For example, since vascular penetration relies to a Certain degree on circulatory status, the technique may be very difficult or impossible in emergency situations where the patient may be in shock or severely dehydrated. Worse, time is typically of the essence in such situations, precluding extended trial and error.

Perhaps the most effective alternative to venous connection is the intra-osseous technique, wherein a needle capable of puncturing the outer cortical layer of a bone is used to penetrate into the osseous or marrow region, where there exists a fresh blood supply. The technique is particularly suited for use with larger bones such as the femur, though alternatives may be used, depending on the circumstances.

Although the procedure has its proponents and detractors, at the present time the technique is regaining in popularity. However, introduction of the needle associated with the intra-osseous procedure is, today, entirely manual. Typically, the physician or nurse fits an intra-osseous type of needle into the end of a ball-shaped handle, as shown in FIG. 1, and screws the needle through the bone and into the intra-osseous region. Turning of the handle may take several rotations, and, particularly in intense emergency situations, the handle can slip off of the needle and cause the bone to chip, crack or cause the point of entry to become too large to function properly. Accordingly, there remains a need to automate procedures associated with the intra-osseous needle introduction.

SUMMARY OF THE INVENTION

The present invention improves upon the current, entirely manual method used in connection with intraosseous procedures by providing a hand-held drill, having a rotatable chuck to which the needle may be removably secured. Rotation of the chuck and needle may be powered electrically, in which case the housing includes a small motor and batteries, preferably rechargeable. The area through which the chuck emerges is preferably sealed, and recharging of the batteries is preferably carried out inductively, so that a hermetic packaging may be used and which is conducive to prolonged sterilization.

In an alternative embodiment, the drill is mechanically powered, including a wind-up mechanism storing sufficient energy for the introduction of a suitable needle. Although this alternative mechanical embodiment requires an initial winding up prior to actual use, it obviates the need for battery changing and/or charging thereof and reduces the risk that the device may be inoperative at a critical time.

Both the electrical and mechanical embodiments preferably further include torque-conversion gearing to reduce rotation of the chuck while increasing power to ensure effective penetration of the cortical layer. The chuck is further adapted to removably secure the needle having needles with standard fittings such as the Luer® types which are in common use throughout the profession.

DETAILED DESCRIPTION OF THE PREFERRED EMBODIMENTS

Figure 1:
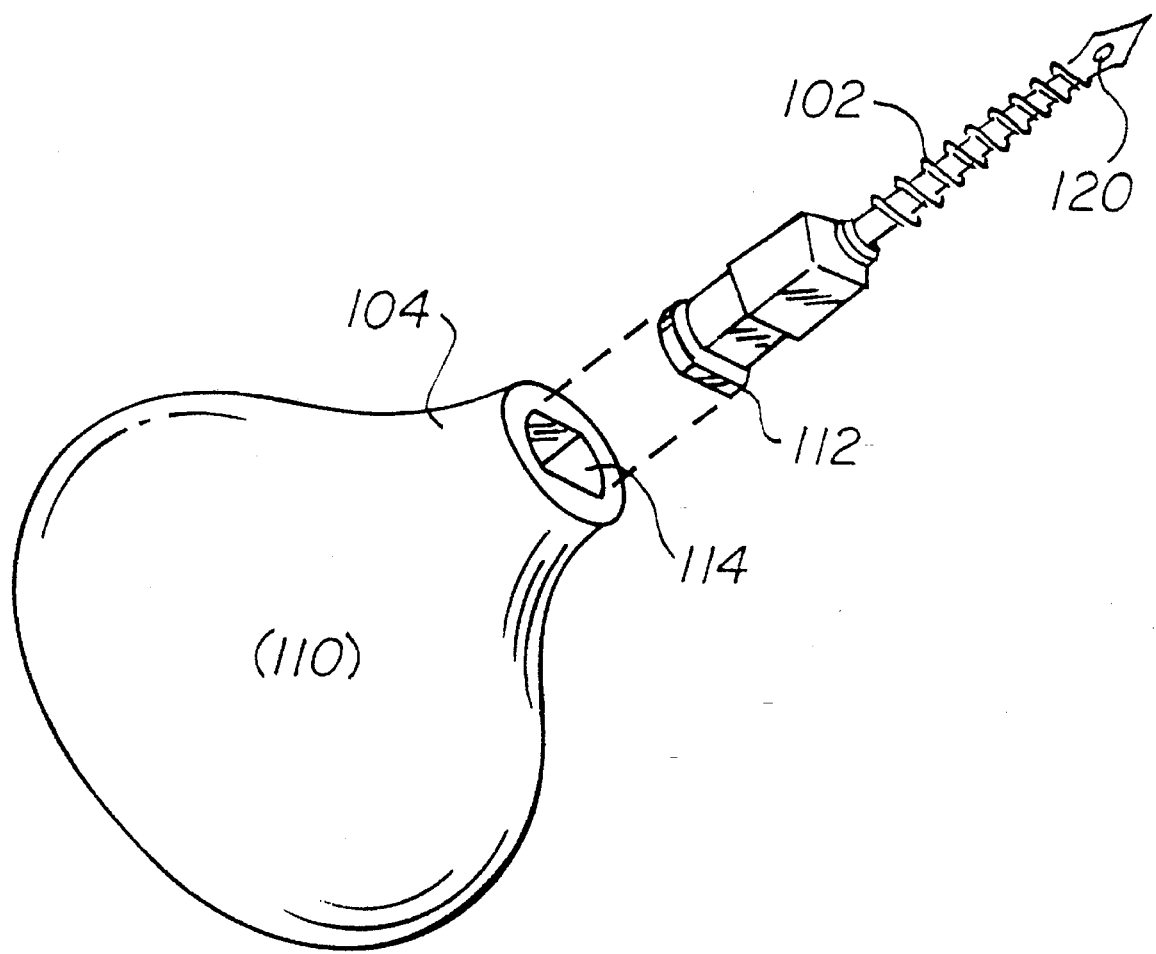
FIG. 1 is a drawing which illustrates an existing intra-osseous needle drill which is introduced using a ball-shaped handle.

FIG. 1 is a drawing of a hand-operated intra-osseous drill, wherein an appropriate needle 102 is fitted into a stem 104 integrally formed with a ball—or oval-shaped handle 110. The needle 102 includes a fitting 112 at its proximal end, typically of the Luer-lock® type in common use, and the receptacle 114 formed in the stem 104 is adapted to engage with the proximal end 112 such that it may be readily slidable received therein, that rotate in cooperation with the handle 110 as it is turned. This physical cooperation is made possible by the fact that the proximal end of the needle 112 is a non-symmetrical in transverse cross-section, and this irregularity allows the needle to slip into the recess 114 and turn with device as a unit during use. The shaft of the needle 102 in one popular configuration includes a hollow structure having an outer sharp spiral shape to facilitate drilling, and an aperture is provided at the distal tip 120 at the needle 102 forming a passage to the hollow interior of the needle. The disadvantages of this manual approach have previously been discussed with reference to the Background of the Invention.

Figure 2:
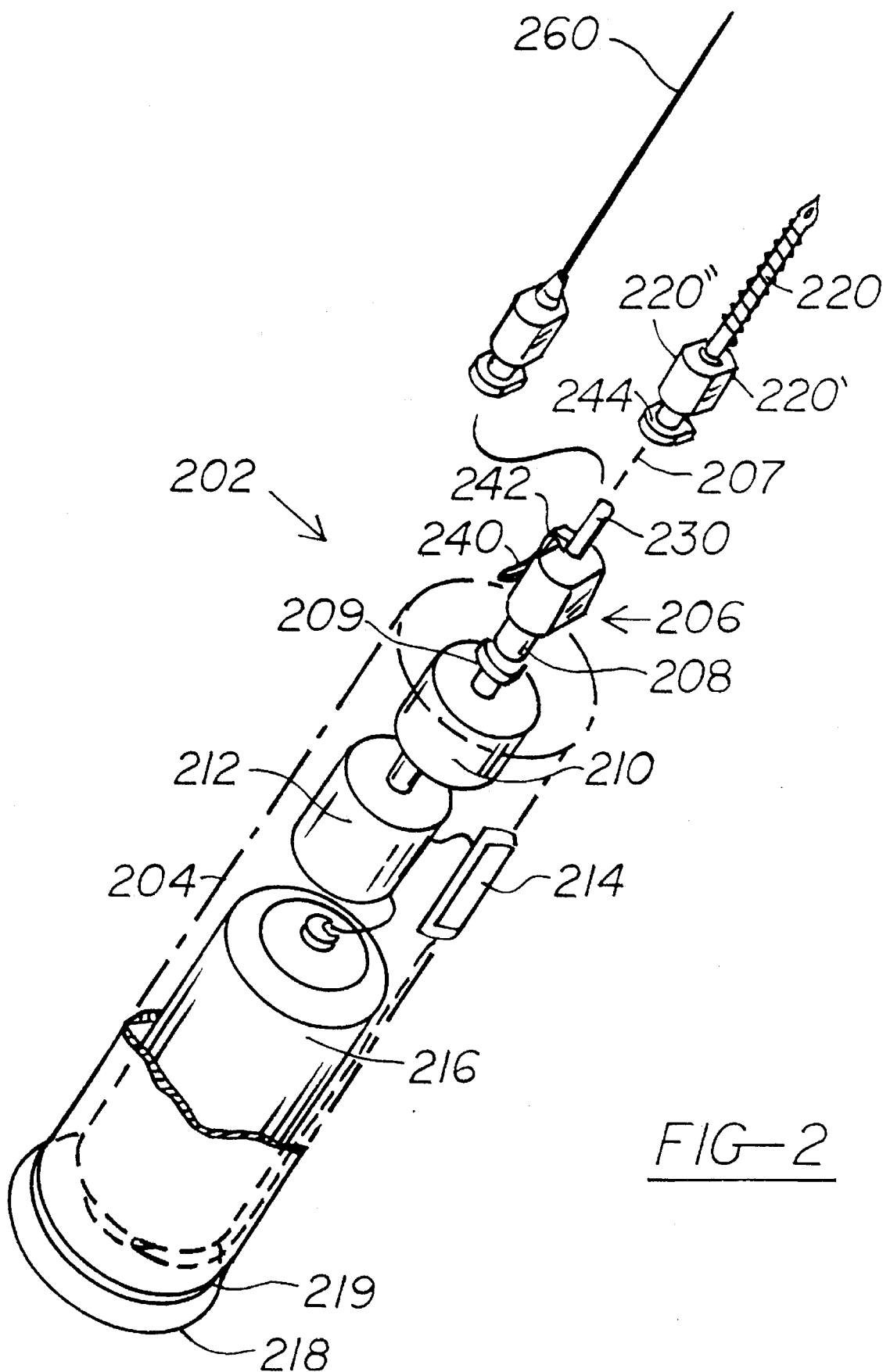
FIG. 2 is a drawing of an electrical version of a drill according to the invention having surfaces removed to reveal internal structures.

FIG. 2 illustrates from an oblique perspective an electrical version of an intra-osseous drill formed according to the invention, depicted generally at 202. A housing 204 suitable for hand-holding is shown in partial phantom outline to reveal important internal components. A specially designed chuck 206 is secured to a shaft 208 rotatable about axis 207 which emerges through the hand-held housing 204 through a seal 209. Alternatively, the chuck itself may emerge from the housing. The shaft 208 is driven by a motor 212 though, in the preferred embodiment, a speed reducer 210 is added so that a less expensive higher-speed DC motor may be used to provide the amount of torque necessary to turn the needle 220 so as to drill through the cortical layer of the bone. The motor is actuated by switch 214 which is internally operatively connected to a battery 216, preferably of the rechargeable variety. Access to the housing is gained by removing a screw-on cap 218, preferably including a seal 219.

A proper charge level of the battery 216 may be maintained by keeping the drill 202 in a suitable charging stand (not shown) such as the type used for flashlights, portable phones, and the like, in which case contacts (not shown) on the bottom outer portion of the cap 218 may be provided for such purpose. Alternatively, an inductive charging mechanism, also not shown, may be included, preferably in the vicinity of cap 218, thereby facilitating a recharge of the battery without having to provide any external electrical contacts. The inductively charged version would therefore include a pick-up coil within the housing along with appropriate electronics associated with power conversion, charge level, and so forth. Such an inductive charging mechanism, in conjunction with seals 209 and 219, are preferably incorporated to provide an overall structure sealed with respect to the environment, preferably in hermetic fashion, so that the entire unit may undergo sterilization and perhaps be packaged in the sterilized form prior to use. As such, in the preferred embodiment, the outer housing 204 and all externally exposed components, would be manufactured of an inert, rust-resistant, non-magnetic material such as stainless steel.

The chuck 206 includes an outward extending stem 230 adapted to for insertion within a corresponding cavity associated with standard needle fittings, including the popular Luer-lock® type of design, which is depicted in the figures. To facilitate quick engagement of the needle 220 with the post 230, the chuck 206 is preferably designed using a non-symmetrical cross section corresponding generally to the cross section used in such standard needle fittings, that is, with an overall circular cross section having two opposing flat surfaces 220' and 220''. Also in the preferred embodiment, the chuck 206 includes a finger-operated, rocker-type latch 240 having an upper tab 242 which releasably engages with the rim 244 of the needle. Thus, a needle may be quickly inserted onto the chuck 206, held in place during drilling, then, by depressing the lower portion of the latch, the needle may be immediately released from the chuck 206 so that syringes, IVs, and so forth, can be connected to the needle. Note that due to the ability of the chuck 206 to accept any type of needle suitable for drilling action, alternative needles may be installed thereupon, including a lumbar puncturing needle 260, or any other needle suitable for the uses described herein.

Figure 3:
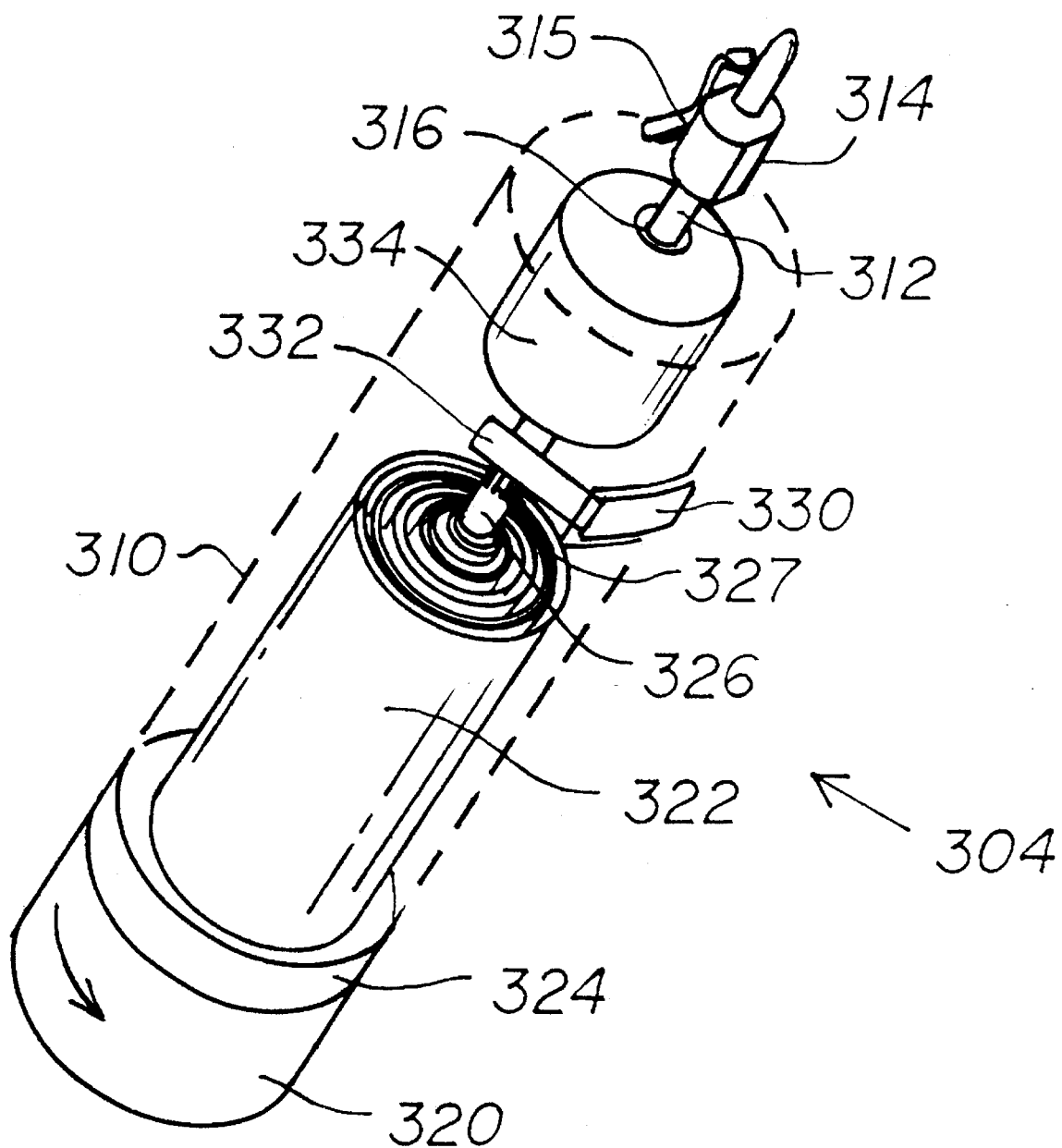
FIG. 3 is an oblique drawing of an alternative, mechanically oriented version of the invention.

FIG. 3 illustrates a mechanical alternative embodiment of the invention depicted generally at 304. Although this version of the device requires winding prior to the use, this slight inconvenience is outweighed by the assurance that the device will operate reliably, particularly in emergency situations, without concern for battery charge level. The overall appearance of the mechanical version is similar to its electrical counterpart, including a cylindrical, hand-held housing 310 depicted partially with phantom lines to indicate major internal components. The shaft 312 emerges from the distal end of the unit, onto which is attached a chuck 314, which may be identical to the chuck 206 shown in FIG. 2, including a manually operated latch mechanism 315 to hold a needle in place during use. As with the electrical version, the shaft 312 emerges from the body of the unit through a seal 316, which may include a bearing.

The proximal end of the mechanical device includes winder 320 which, when turned in a particular direction, causes spring 322 to store potential energy by virtue of a ratchet 324 disposed between the winder 320 and an outer surface of the spring 322. The inner portion of the spring 322 is connected lengthwise to shaft 326, the rotation of which is halted by ridges 327 formed circumferentially around a portion of the shaft as shown in the figure. After having sufficiently wound the device at its proximal end, the potential energy is converted to kinetic energy by depression of pushbutton 330 which includes an arm 332 integrally attached thereto having a release mechanism which engage with the grooves 327 on the shaft 326 until such time that the button 330 is activated. Upon such activation, the arm 332 moves away from the shaft, thereby releasing energy, ultimately to rotate the chuck 314 and attached needle. Also in this mechanical version, a reducer 334 is preferably included to convert the high torque available at shaft 326 into a lower speed but higher powered turning of the shaft 312, chuck and needle.

Having thus described my invention, I claim:

1. A drill and medical needle assembly, comprising:

a needle having a fitting end and a tip suitable for intra-osseous use, the fitting end of the needle featuring a primarily circular but non-symmetrical cross-section including two opposing flat outer surfaces, the drill comprising:

a hand-held housing having proximal and distal ends;

a chuck to removably receive the needle at its fitting end, the chuck being rotatable and extending outwardly from the distal end of the housing, the physical mounting of the chuck being sufficiently close to the distal end of the housing to minimize lateral movement of the chuck and needle attached thereto during the rotation thereof, the chuck including means for releasably receiving and mating with the fitting end of the needle;

energy storage means disposed within the housing and coupled in an energy path to the chuck, the energy released from the energy storage means being sufficient to permit the rotating needle to penetrate into the intra-osseous cavity of a patient; and a user-accessible switch supported on the housing, the activation of which causes at least a portion of the stored energy to be converted into the rotation of the chuck and medical needle.

2. The needle drill of claim 1, further including:

energy storage means in the form of a battery;

a motor having a shaft mechanically coupled to the chuck, and wherein the switch is electrical and includes operative connections among the switch, motor, and battery.

3. The needle drill of claim 2, including a rechargeable battery.

4. The needle drill of claim 2, further including an inductive pick-up within the housing and power-conversion circuitry enabling the battery to be inductively charged.

5. The needle drill of claim 2, further including torque-conversion means disposed between the shaft of the motor and the chuck to increase rotational power available at the needle.

6. The needle drill of claim 2, further including torque-conversion means disposed between the shaft of the motor and the chuck to increase rotational power available at the needle.

7. The needle drill of claim 1, further including mechanical energy storage means in the form of a wind-up spring mechanically coupled to the chuck, and wherein the switch allows energy stored in the spring to be released to rotate the chuck and needle attached thereto.

8. The needle drill of claim 7, further including:

a first ratcheting mechanism coupling energy from a wind-up mechanism to the spring; and a release mechanism coupled to the switch which allows the spring to receive and store energy during the wind-up thereof and which further allows the stored energy to be subsequently released to the chuck and needle upon activation of the switch.

9. The needle drill of claim 7, wherein the spring is of the spirally wound type.

10. The needle drill of claim 7, further including torque-conversion means disposed between the second end of the spring and the chuck to increase rotational power available at the needle.

11. The needle drill of claim 1, the areas of the housing associated with the chuck and switch including moisture-impermeable seals to enhance the sterilizability of the drill overall.

* * * * *